US009568726B2

(12) United States Patent
Kamo et al.

(10) Patent No.: US 9,568,726 B2
(45) Date of Patent: Feb. 14, 2017

(54) OBJECTIVE OPTICAL SYSTEM FOR ENDOSCOPE (71) Applicant: OLYMPUS CORPORATION, Hachioji-shi, Tokyo (JP)

(72) Inventors: Yuji Kamo, Hino (JP); Shinya Sato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/216,249

(22) Filed: Jul. 21, 2016

(65) Prior Publication Data
US 2016/0327780 A1 Nov. 10, 2016

Related U.S. Application Data (63) Continuation of application No. PCT/JP2015/064582, filed on May 21, 2015.

(30) Foreign Application Priority Data

Jun. 20, 2014 (JP) ................................ 2014-127318

(51) Int. Cl.
G02B 23/24 (2006.01)
G02B 13/04 (2006.01)
(Continued)

(52) U.S. Cl.
CPC ......... *G02B 23/243* (2013.01); *A61B 1/00188* (2013.01); *G02B 9/60* (2013.01); *G02B 13/04* (2013.01)

(58) Field of Classification Search
CPC ......... G02B 13/14; G02B 13/04; G02B 13/06; G02B 9/60; G02B 9/62; G02B 23/243; G02B 23/2438
(Continued)

(56) References Cited

U.S. PATENT DOCUMENTS 8,456,767 B2 * 6/2013 Takato ................. G02B 23/243
359/753
8,773,765 B2 * 7/2014 Sasamoto ................ G02B 7/08
359/649
(Continued)

FOREIGN PATENT DOCUMENTS

JP 2007233036 A 9/2007
JP 4934233 B2 5/2012
(Continued)

OTHER PUBLICATIONS

International Search Report (ISR) dated Jul. 21, 2015 and Written Opinion issued in International Application No. PCT/JP2015/064582.

*Primary Examiner* — Zachary Wilkes
(74) *Attorney, Agent, or Firm* — Holtz, Holtz & Volek PC (57) ABSTRACT A small-sized objective optical system for an endoscope having in order from an object side, a first negative lens which is planoconcave, a second meniscus lens having a convex surface directed toward an image side, a third positive meniscus lens having a convex surface directed toward the object side, a positive lens unit, and a cemented lens in which, a positive lens and a negative lens are cemented. Focusing is carried out by moving the third positive meniscus lens along an optical axis, and the second meniscus lens is a negative lens.

10 Claims, 9 Drawing Sheets (51) Int. Cl.
  *G02B 9/60* (2006.01)
  *A61B 1/00* (2006.01)
(58) Field of Classification Search
  USPC .................................. 359/753, 770, 659, 649
  See application file for complete search history.

(56) References Cited

U.S. PATENT DOCUMENTS

| | | |
|---|---|---|
| 9,106,848 B2 * | 8/2015 | Kamo .................. G02B 23/243 |
| 2007/0206293 A1 | 9/2007 | Takato |
| 2012/0057251 A1 | 3/2012 | Takato |
| 2013/0155212 A1 | 6/2013 | Kamo |
| 2013/0217965 A1 | 8/2013 | Sasamoto |
| 2015/0268460 A1 | 9/2015 | Takada |

FOREIGN PATENT DOCUMENTS

| | | |
|---|---|---|
| WO | 2011070930 A1 | 6/2011 |
| WO | 2012169369 A1 | 12/2012 |
| WO | 2013021744 A1 | 2/2013 |
| WO | 2014088104 A1 | 6/2014 |
| WO | 2015064614 A1 | 5/2015 |

\* cited by examiner

OBJECTIVE OPTICAL SYSTEM FOR ENDOSCOPE

CROSS-REFERENCE TO RELATED APPLICATION

The present application is a continuation of PCT/JP2015/064582, filed on May 21, 2015 which is based upon and claims the benefit of priority from Japanese Patent Application No. 2014-127318 filed on Jun. 20, 2014; the entire contents of which are incorporated herein by reference.

FIELD OF THE INVENTION

The present invention relates to an objective optical system such as an objective optical system that can be used in an endoscope apparatus to be used in fields such as a medical field and an industrial field.

DESCRIPTION OF THE RELATED ART

An endoscope is an apparatus that has been used widely in a medical field and an industrial field. In the medical field, images of various parts in a body cavity are achieved by an endoscope inserted inside the body cavity. Diagnosis of apart observed, is made by using these images. In such manner, endoscopes have been used for the observation of various parts in the body cavity and diagnosis.

In the observation by an endoscope, it is desirable that focused images in a wide range from a near point to a far point are captured. In this case, generally, an observation depth is determined by an F-number (hereinafter, referred to as 'Fno'). Consequently, the observation depth has limitations.

Therefore, in recent years, an image forming optical system which enables to carry out observation with wider observation depth has been proposed. In such image forming optical system, zoom and focus are used. As an image forming optical system having a focus function (hereinafter, referred to as "focusing optical system"), an objective optical system in Japanese Patent No. 4934233 Publication is available.

SUMMARY OF INVENTION

The present invention provides the following means. An objective optical system for endoscope comprising in order from an object side:
a first negative lens which is planoconcave;
a second meniscus lens having a convex surface directed toward an image side;
a third positive meniscus lens having a convex surface directed toward the object side;
a positive lens unit; and
a cemented lens in which, a positive lens and a negative lens are cemented, wherein
focusing is carried out by moving the third positive meniscus lens along an optical axis, and
the second meniscus lens is a negative lens, and
the objective optical system for endoscope satisfies the following conditional expression (1), and satisfies at least one of the following conditional expressions (4-1) and (4-2)

$$2.3 \le fp/Ih \le 5 \quad (1)$$

$$-1.5 \le r2/r3 \le -0.28 \quad (4\text{-}1)$$

$$-0.2 \le r2/r4 \le -0.08 \quad (4\text{-}2)$$

where,
fp denotes a focal length of the positive lens unit, and
Ih denotes the maximum image height of the objective optical system for endoscope,
r2 denotes an image-side radius of curvature of the first negative lens,
r3 denotes an object-side radius of curvature of the second meniscus lens, and
r4 denotes an image-side radius of curvature of the second meniscus lens.

BRIEF DESCRIPTION OF THE DRAWINGS

FIG. 1A and FIG. 1B are diagrams showing a cross-sectional arrangement of an objective optical system for endoscope according to an embodiment of the present invention, where, FIG. 15 is a cross-sectional view in a close observation state.

FIG. 2A and FIG. 2B are diagrams showing a cross-sectional arrangement of an objective optical system for endoscope according to an example 1 of the present invention, where, FIG. 25 is a cross-sectional view in a close observation state;

FIG. 3A, FIG. 3B, FIG. 3C, FIG. 3D, FIG. 3E, FIG. 35, FIG. 30, and FIG. 3H are aberration diagrams showing a spherical aberration (SA), an astigmatism (AS), a distortion (DT), and a chromatic aberration of magnification (CC) respectively, of the example 1;

FIG. 4A and FIG. 4B are diagrams showing a cross-sectional arrangement of an objective optical system for endoscope according to an example 2 of the present invention, where.

FIG. 6A and FIG. 6B are diagrams showing a cross-sectional arrangement of an objective optical system for endoscope according to an example 3 of the present invention, where.

FIG. 8A and FIG. 8B are diagrams showing a cross-sectional arrangement of an objective optical system for endoscope according to an example 4 of the present invention, where.

DETAILED DESCRIPTION OF THE INVENTION

Reasons for adopting such arrangement for an objective optical system for endoscope according to the present embodiment and effects thereof will be described below by using diagrams. However, the present invention is not restricted to the following embodiments.

Figure 1A:
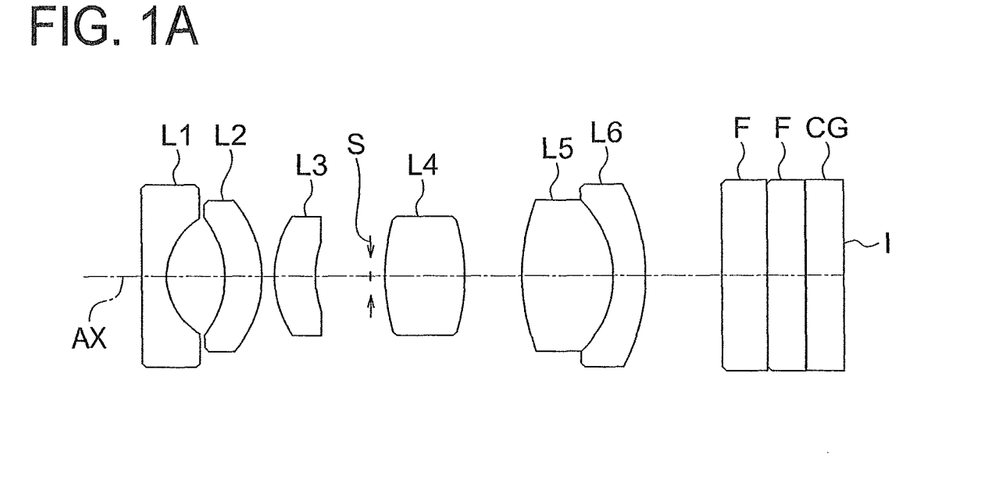
FIG. 1A is a cross-sectional view in a normal observation state.
Figure 1B:
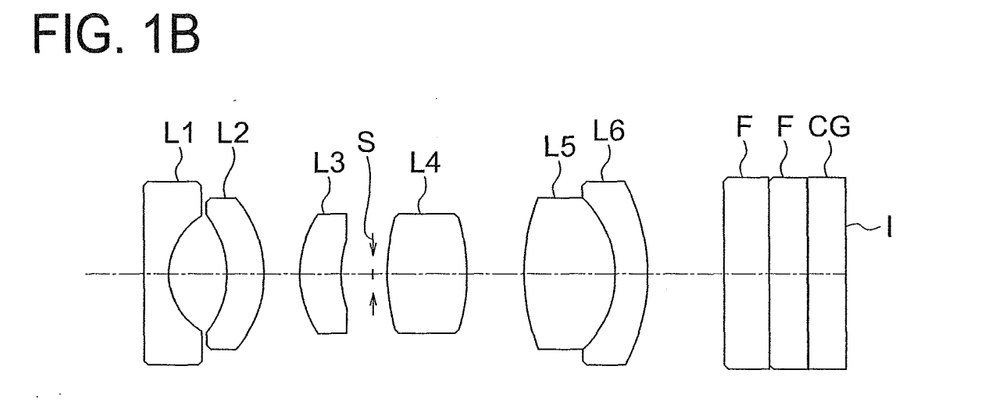

FIG. 1A and FIG. 1B are diagrams showing a cross-sectional arrangement of the objective optical system for endoscope according to the present embodiment. Here, FIG. 1A is a diagram showing a cross-sectional arrangement of the objective optical system for endoscope in a normal observation state, and FIG. 1B is a diagram showing a cross-sectional arrangement of the objective optical system for endoscope in a close observation state.

In the objective optical system for endoscope (hereinafter, referred to as 'objective optical system') according to the present embodiment, for realizing an objective optical system with a small size and a superior performance which can be used in an endoscope, first of all, a first negative lens L1 is disposed nearest to an object. Accordingly, it is made possible to adopt an arrangement of a retro focus type as an arrangement of the objective optical system.

Besides, the first negative lens L1 is let to be a plano-concave lens, and also, the first negative lens L1 is disposed such that a flat surface is directed toward an object side. By making such arrangement, removal of water during observation is improved, and breaking of a lens due to an impact is reduced.

Moreover, a second meniscus lens L2 is disposed on the image side of the first negative lens L1. Furthermore, the shape of the second meniscus lens L2 is let to be a meniscus shape with a convex surface directed toward the image side. By making such arrangement, a lens diameter is suppressed from becoming large, while correcting an aberration of the first negative lens L1.

Furthermore, a focusing unit in which, a lens moves is disposed on the image side of the second meniscus lens L2. More specifically, a third positive meniscus lens L3 is disposed as the focusing unit. At the time of focusing, the third positive meniscus lens L3 is moved along an optical axis. Moreover, to suppress an aberration fluctuation due to the movement of the lens at the time of focusing, a shape of the third positive meniscus lens L3 is let to be a meniscus shape having a convex surface directed toward the object side.

A fourth positive lens unit L4 is disposed on the image side of the third positive meniscus lens L3. The fourth positive lens unit L4 contributes mainly to image formation. Therefore, a light beam is converged by a positive refractive power of the fourth positive lens unit L4.

On the image side of the fourth positive lens unit L4, an axial light beam and an off-axis light beam get separated. Therefore, a cemented lens is disposed on the image side of the fourth positive lens unit L4. The cemented lens includes a fifth positive lens L5 and a sixth negative lens L6. When such an arrangement is made, the cemented lens including the fifth positive lens L5 and the sixth negative lens L6 is disposed at a position at which, a height of a light ray of the off-axis light beam becomes high. Accordingly, it is possible to correct a chromatic aberration favorably. It is possible to let the sixth negative lens L6 to be a negative meniscus lens having a convex surface directed toward the image side.

Generally, when an Fno of an optical system becomes fast, an amount of a spherical aberration and a coma that occur, becomes large. Consequently, when the Fno of an optical system is made fast, it is disadvantageous for correction of the spherical aberration and the coma.

Here, in the objective optical system of the present embodiment, the main positive refractive power is secured as a refractive power of lens units disposed on the image side of the third positive meniscus lens L3, or in other words, the positive refractive power of the fourth positive lens unit L4 and the positive refractive power of the fifth positive lens L5 in the cemented lens. Therefore, when the Fno of the optical system is made fast, an aberration is susceptible to occur in the fourth positive lens unit L4 and the fifth positive lens L5.

Moreover, also the positive refractive power that is necessary for realizing the arrangement of the retro focus type is achieved by the fourth positive lens unit L4 and the fifth positive lens L5. Consequently, the positive refractive power of the fourth positive lens unit L4 and the positive refractive power of the fifth positive lens L5 are related to the size of the objective optical system.

Particularly, the fourth positive lens unit L4 is disposed on the object side of the fifth positive lens L5, here, the height of an axial light ray becomes higher at the fourth positive lens unit L4 than the height at the fifth positive lens L5. Consequently, an effect of aberration is more at the fourth positive lens unit L4 where the height of the axial light ray is high.

On the other hand, for a positive lens which is not cemented, it is easy to secure the necessary refractive power, and a contribution to the size of the optical system is also high. Therefore, it is preferable to set appropriately a focal length of the fourth positive lens unit L4.

For such reasons, in the objective optical system according to the present embodiment, it is desirable to satisfy the following conditional expression (1)

$$2.3 \leq fp/Ih \leq 5 \qquad (1)$$

where, fp denotes a focal length of the fourth positive lens unit L4, and

Ih denotes the maximum image height of the objective optical system for endoscope.

When exceeding an upper limit value of conditional expression (1), the positive refractive power of the fourth positive lens unit L4 becomes excessively small. In this case, the overall length of the optical system becomes large. Consequently, small-sizing of the optical system cannot be met.

When falling below a lower limit value of conditional expression (1), the positive refractive power of the fourth positive lens unit L4 becomes excessively large with respect to the Fno. In this case, the spherical aberration and the coma are deteriorated. Consequently, it is not possible to secure a superior optical performance.

It is desirable to satisfy the following conditional expression (1') instead of conditional expression (1).

$$2.4 \leq fp/Ih \leq 4 \qquad (1')$$

Furthermore, it is desirable to satisfy the following conditional expression (1") instead of conditional expression (1).

$$2.5 \leq fp/Ih \leq 3.5 \qquad (1'')$$

As a refractive power of the first negative lens L1, for realizing the arrangement of retro focus type, a comparatively large negative refractive power is necessary. Here, when the negative refractive power is made too large, the coma is deteriorated. Therefore, it is preferable to set the refractive power of the first negative lens unit L1 appropriately. By making such arrangement, even in an objective optical system with a comparatively fast Fno, such as the objective optical system according to the present embodiment, it is possible to have a favorable aberration balance in the overall optical system.

For such reasons, in the objective optical system according to the present embodiment, it is desirable to satisfy the following conditional expression (2).

$$-2 \leq f1/Ih \leq -0.9 \quad (2)$$

where, f1 denotes a focal length of the first negative lens L1, and

Ih denotes the maximum image height of the objective optical system for endoscope.

When exceeding an upper limit value of conditional expression (2), the negative refractive power of the first negative lens L1 becomes excessively large. In this case, the coma and an astigmatism are not corrected adequately. Consequently, the optical performance is degraded.

When falling below a lower limit value of conditional expression (2), the negative refractive power of the first negative lens unit L1 becomes excessively small. In this case, the overall length of the optical system becomes excessively large. Consequently, a condition of small-sizing which is necessary as an objective optical system for endoscope cannot be fulfilled.

It is desirable to satisfy the following conditional expression (2') instead of conditional expression (2).

$$-1.6 \leq f1/Ih \leq -0.9 \quad (2')$$

Furthermore, it is desirable to satisfy the following conditional expression (2") instead of conditional expression (2).

$$-1.2 \leq f1/Ih \leq -0.9 \quad (2'')$$

Moreover, the fifth positive lens L5 in the cemented lens, while contributing to securing the overall positive refractive power, also contributes to the correction of chromatic aberration by being cemented with the sixth negative lens L6.

For such reason, in the objective optical system according to the present embodiment, it is desirable to satisfy the following conditional expression (3) in at least one of a normal observation state and a close observation state.

$$-3 \leq (fc1 \times fc2)/(fc \times f) \leq -0.85 \quad (3)$$

where, fc1 denotes a focal length of the fifth positive lens L5 in the cemented lens, fc2 denotes a focal length of the sixth negative lens L6 in the cemented lens, fc denotes a combined focal length of the cemented lens, and f denotes a focal length of the overall objective optical system for endoscope.

When exceeding an upper limit value of conditional expression (3), either the spherical aberration and the comma aberration are deteriorated, or correction of a chromatic aberration of magnification becomes insufficient.

When falling below a lower limit value of conditional expression (3), either the overall length of the optical system becomes excessively large, or the correction of the chromatic aberration of magnification becomes excessive.

It is desirable to satisfy the following conditional expression (3') instead of conditional expression (3)

$$-2.3 \leq (fc1 \times fc2)/(fc \times f) \leq -0.88 \quad (3')$$

Furthermore, it is desirable to satisfy the following conditional expression (3") instead of conditional expression (3).

$$-1.7 \leq (fc1 \times fc2)/(fc \times f) \leq -0.9 \quad (3'')$$

Moreover, when an attempt is made to secure the negative refractive power, which is necessary for realizing the arrangement of the retro focus type, only by the first negative lens L1, since the first negative lens L1 has a large negative refractive power, a substantial aberration occurs. Therefore, it is preferable to make the refractive power of the second meniscus lens L2 to be disposed on the image side thereof, to be a negative refractive power. Thus, it is necessary to divide the negative refractive power between the first negative lens L1 and the second meniscus lens L2, as well as to correct favorably the astigmatism and the coma in a peripheral area of screen.

For such reasons, in the objective optical system according to the present embodiment, it is desirable to satisfy the following conditional expressions (4-1) and (4-2)

$$-1.5 \leq r2/r3 \leq -0.28 \quad (4-1)$$

$$-0.2 \leq r2/r4 \leq -0.08 \quad (4-2)$$

where, r2 denotes an image-side radius of curvature of the first negative lens L1, r3 denotes an object-side radius of curvature of the second meniscus lens L2, and r4 denotes an image-side radius of curvature of the second meniscus lens L2.

When exceeding upper limit values of conditional expressions (4-1) and (4-2), either a correction effect with respect to the astigmatism and the coma is degraded, or an amount of aberration that occurs in the first negative lens L1 becomes excessively large, and all the aberrations are deteriorated.

When falling below lower limit values of conditional expressions (4-1) and (4-2), either the correction of the astigmatism and the coma becomes excessive, or the overall length of the optical system becomes excessively large.

It is desirable to satisfy the following conditional expressions (4-1') and (4-2') instead of conditional expressions (4-1) and (4-2).

$$-1 \leq r2/r3 \leq -0.3 \quad (4-1')$$

$$-0.15 \leq r2/r4 \leq -0.09 \quad (4-2')$$

Furthermore, it is desirable to satisfy the following conditional expressions (4-1") and (4-2") instead of conditional expressions (4-1) and (4-2).

$$-0.75 \leq r2/r3 \leq -0.32 \quad (4-1'')$$

$$-0.13 \leq r2/r4 \leq -0.1 \quad (4-2'')$$

Moreover, in the third positive meniscus lens l3 or in an optical system disposed on the image side of an aperture stop S, it s necessary to secure the positive refractive power which is associated mainly with image formation. For this, for the fourth positive lens unit L4 and the cemented lens, it is desirable to set a ratio of focal lengths that would enable to correct favorably the spherical aberration and the coma, while taking into consideration shortening the overall length and securing back focus.

For such reasons, in the objective optical system according to the present embodiment, it is desirable to satisfy the following conditional expression (5).

$$0.45 \leq fp/fc \leq 1.3 \quad (5)$$

where, fp denotes the focal length of the fourth positive lens unit 14, and fc denotes a combined focal length of the cemented lens.

When exceeding an upper limit value of conditional expression (5), either the overall length of the optical system becomes excessively large, or occurrence of the coma due to the cemented lens cannot be corrected fully.

When falling below a lower limit value of conditional expression (5), either the back focus is excessively short thereby making the assembling impossible, or the spherical aberration which occurs due to the fourth positive lens unit L4 cannot be corrected fully.

It is desirable to satisfy the following conditional expression (5') instead of conditional expression (5).

$$0.47 \leq fp/fc \leq 1.1 \quad (5')$$

Furthermore, it is desirable to satisfy the following conditional expression (5") instead of conditional expression (5)

$$0.45 \leq fp/fc \leq 0.9 \quad (5'')$$

As mentioned above, in the objective optical system according to the present embodiment, the arrangement of the retro focus type is realized by the lens having a negative refractive power which is disposed on the object side and the lens having a positive refractive power which is disposed on the image side. Accordingly, small-sizing of the optical system is facilitated while correcting the astigmatism and the coma.

Here, particularly, an arrangement of the first negative lens L1 and a predetermined optical system is significant for small-sizing and for maintaining the aberration balance of the overall objective optical system. The predetermined optical system refers to an optical system formed by combining the fourth positive lens unit L4 and the cemented lens (the fifth positive lens L5 and the sixth negative lens L6)

For such reasons, in the objective optical system according to the present embodiment, it is desirable to satisfy the following conditional expression (6)

$$-5 \leq fpc/f1 \leq -2 \quad (6)$$

where, fpc denotes a combined focal length of the fourth positive lens unit L4 and the cemented lens, and f1 denotes a focal length of the first negative lens L1.

When exceeding an upper limit value of conditional expression (6), the refractive power of the first negative lens unit L1 becomes excessively small. Accordingly, either a diameter of the optical system becomes large or the refractive power of the predetermined optical system becomes excessively large, and the spherical aberration and the coma are deteriorated.

When falling below a lower limit value of conditional expression (6), the refractive power of the first negative lens unit becomes excessively large. Accordingly, either the aberration as a whole is deteriorated, or the refractive power of the predetermined optical system becomes excessively small, and the overall length of the optical system becomes large, It is desirable to satisfy the following conditional expression (6') instead of conditional expression (6).

$$-4 \leq fpc/f1 \leq -2.1 \quad (6')$$

Furthermore, it is desirable to satisfy the following conditional expression (6") instead of conditional expression (6).

$$-3.2 \leq fpc/f1 \leq -2.2 \quad (6'')$$

Moreover, the third positive meniscus lens L3 moves as a focusing lens at the time of focusing. Consequently, in the third positive meniscus lens L3, an aberration fluctuation due to focusing is susceptible to occur. Moreover, when the lens moves, the lens is tilted and shifted, and deviation of the practical optical system from an original ideal design state cannot be avoided. Consequently, it becomes necessary to set appropriately a focal length of the focusing lens with respect to an amount of movement of lens due to focusing.

For such reason, in the objective optical system according to the present embodiment, it is desirable to satisfy the following conditional expression (7).

$$22 \leq f3/df \leq 50 \quad (7)$$

where, f3 denotes a focal length of the third positive meniscus lens L3, and df denotes the maximum amount of movement of the third positive meniscus lens L3.

When exceeding an upper limit value of conditional expression (7), an amount of movement of the focusing lens becomes excessively large. Consequently, the objective optical system becomes large-sized.

When falling below a lower limit value of conditional expression (7), an amount of aberration occurring due to focusing and variability, or in other words, a manufacturing error becomes large. Consequently, the optical performance of the optical system is degraded.

It is desirable to satisfy the following conditional expression (7') instead of conditional expression (7).

$$22 \leq f3/df \leq 40 \quad (7')$$

Furthermore, it is desirable to satisfy the following conditional expression (7") instead of conditional expression (7).

$$22 \leq f3/df \leq 35 \quad (7'')$$

As mentioned above, when an attempt is made to secure the negative refractive power which is necessary for realizing the arrangement of retro focus type only by the first negative lens L1, the first negative lens L1 has to bear a large negative refractive power. Therefore, in the objective optical system according to the present embodiment, the negative refractive power is divided between the first negative lens L1 and the second meniscus lens L2 as mentioned above.

Here, although the negative refractive power is divided, the first negative lens L1 still has a large negative refractive power, and an optical system of the retro focus type is formed. However, since the first negative lens L1 has a large negative refractive power, a substantial aberration occurs in the first negative lens L1.

In such case, correcting an aberration such as the coma by the third positive meniscus lens L3 having a positive refractive power becomes effective. Particularly, a difference in an image ray height at the first negative lens L1 and at the third positive meniscus lens L3 affects the aberration correction. Therefore, it is preferable to maintain an appropriate distance between the first negative lens L1 and the third positive meniscus lens L3.

For such reasons, in the objective optical lens according to the present embodiment, it is desirable to satisfy the following conditional expression (8).

$$1.35 \leq \Sigma d(L1-L3)/Ih \leq 3 \quad (8)$$

where, $\Sigma d$ (L1–L3) denotes the minimum axial distance from an object-side surface of the first negative lens L1 up to an object-side surface of the third positive meniscus lens L3, and Ih denotes the maximum image height of the objective optical system for endoscope.

When exceeding an upper limit value of conditional expression (8), either a diameter of the first negative lens L1 becomes excessively large, or an amount of movement of the third positive meniscus lens L3 becomes large. Consequently, small-sizing of the first negative lens L1 and the third positive meniscus lens L3 cannot be achieved.

When falling below a lower limit value of conditional expression (8), the refractive power of the first negative lens L1 and the third positive meniscus lens L3 becomes excessively large. Consequently, the coma is deteriorated.

It is desirable to satisfy the following conditional expression (8') instead of conditional expression (8)

$$1.4 \leq \Sigma d(L1-L3)/Ih \leq 2.5 \quad (8')$$

Furthermore, it is desirable to satisfy the following conditional expression (8") instead of conditional expression (8).

$$1.5 \leq \Sigma d(L1-L3)/Ih \leq 2 \quad (8'')$$

Moreover, in the objective optical system according to the present embodiment, it is desirable to satisfy the following conditional expression (9)

$$4 \leq Fno \leq 7 \quad (9)$$

where,

Fno denotes an F-number for the objective optical system for endoscope.

When exceeding an upper limit value of conditional expression (9), there is an effect of diffraction with respect to a pixel pitch of a CCD (charge coupled device).

When falling below a lower limit value of conditional expression (9), the aberration remained becomes excessively large, and also superior optical performance cannot be achieved.

It is desirable to satisfy the following conditional expression (9') instead of conditional expression (9).

$$4.5 \leq Fno \leq 6.6 \quad (9')$$

Furthermore, it is desirable to satisfy the following conditional expression (9") instead of conditional expression (9).

$$5 \leq Fno \leq 6.3 \quad (9'')$$

Moreover, in the objective optical system according to the present embodiment, it is desirable that only the third positive meniscus lens L3 moves at the time of focusing. It is preferable to make such arrangement, as a mechanical arrangement becomes simple.

Moreover, in the objective optical system according to the present embodiment, it is desirable that an aperture stop S is disposed on the image side of the third positive meniscus lens L3. It is preferable to make such arrangement, as it enables to have an aberration balance of the coma and the chromatic aberration of magnification.

Moreover, in the objective optical system according to the present embodiment, the fourth positive lens unit L4 may include a plurality of lenses.

Example 1

An objective optical system for endoscope according to an example 1 will be described below.

Figure 2A:
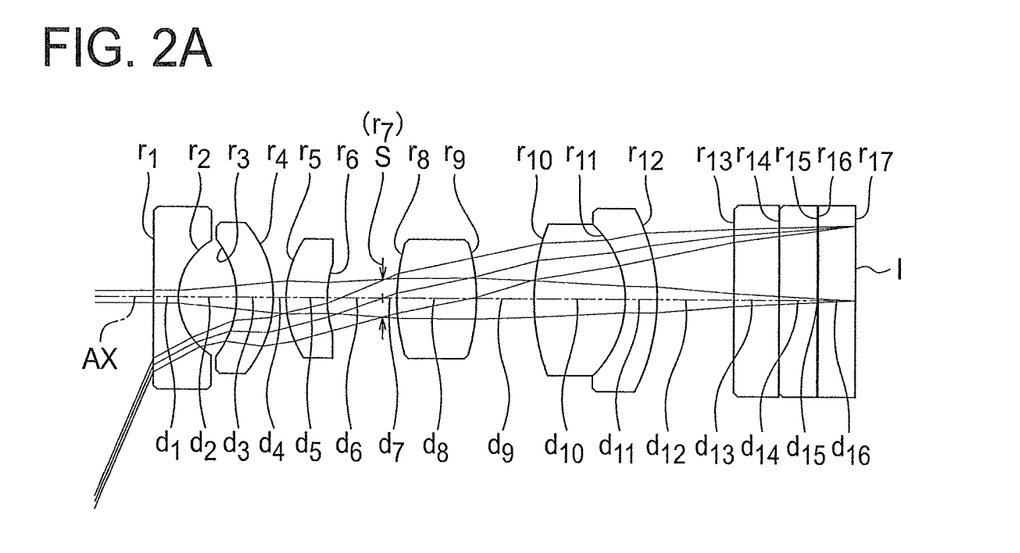
FIG. 2A is a cross-sectional view in a normal observation state.
Figure 2B:
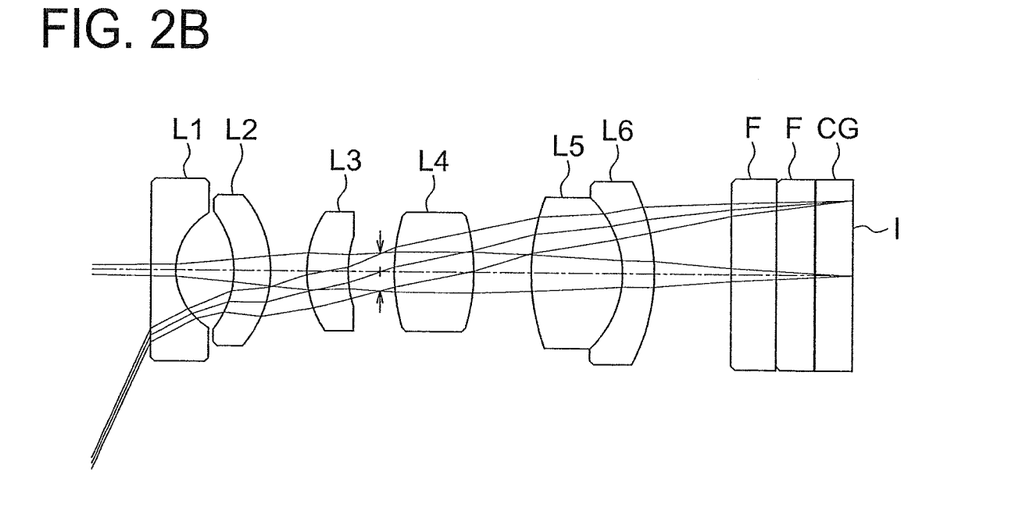
Figure 3A:
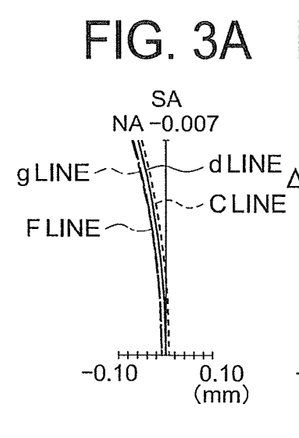
Figure 3B:
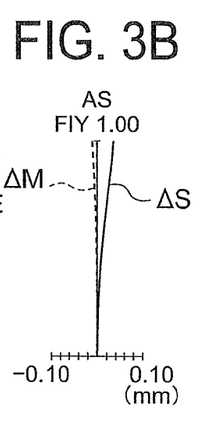
Figure 3C:
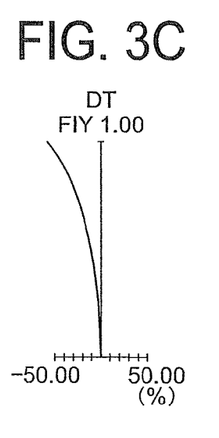
Figure 3D:
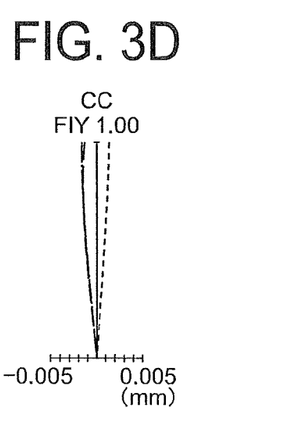
Figure 3E:
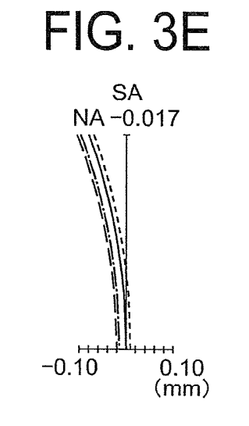
Figure 3F:
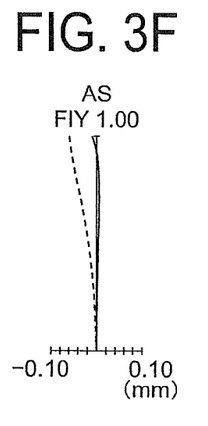
Figure 3G:
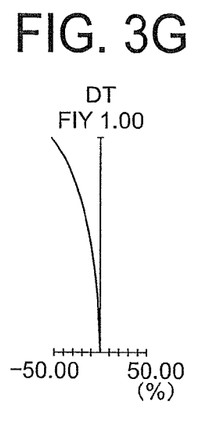
Figure 3H:
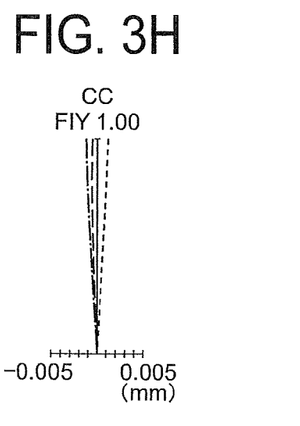

FIG. 2A is a cross-sectional view in a normal observation state (object point at a long distance) of the objective optical system for endoscope according to the present example, and FIG. 2B is a cross-sectional view in a close observation state (object point at a close distance) of the objective optical system for endoscope according to the present example.

In the example 1, an arrangement includes in order from an object side, a first negative lens L1 which is planoconcave, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red absorbing filter F, a cover glass F, and a COD cover glass CG.

The fifth positive lens L5 and the sixth negative meniscus lens L6 are cemented. Moreover, the cover glass F and the COD cover glass CG are cemented. Here, d15 denotes an adhesive layer. Furthermore, a YAG laser cut coating is applied to an object side of the infra-red absorbing filter and an LD laser cut coating is applied to an image side of the infra-red absorbing filter. Furthermore, the third positive meniscus lens L3, at the time of focusing from the normal observation state (FIG. 2A) to the close observation state (FIG. 2B), moves toward the image (image plane I) side.

FIG. 3A, FIG. 3B, FIG. 3C, and FIG. 3D show a spherical aberration (SA), an astigmatism (AS), a distortion (DT), and a chromatic aberration of magnification (CC) in the normal observation state of the present example.

FIG. 3E, FIG. 3S, FIG. 3G, and FIG. 3H show a spherical aberration (SA), an astigmatism (AS), a distortion (DT), and a chromatic aberration of magnification (CC) in the close observation state of the present example.

These aberration diagrams are shown for wavelengths of 65627 nm (C-line), 587.56 nm (d-line), 486.13 nm (F-line), and 435.84 nm (g-line). Moreover, in each diagram, 'FIY' denotes the maximum image height. Similar is the case for the following aberration diagrams.

Example 2

An objective optical system for endoscope according to an example 2 will be described below.

Figure 4A:
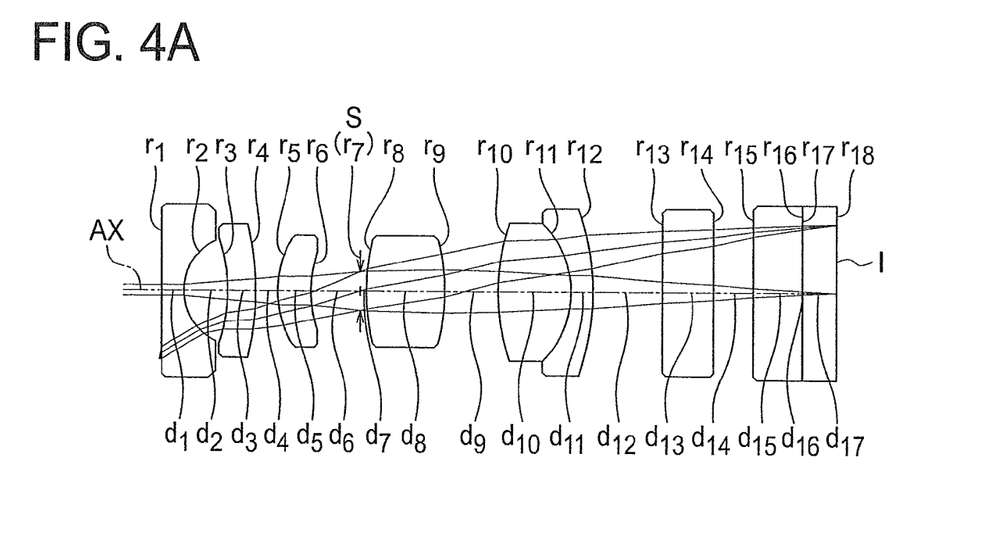
FIG. 4A is a cross-sectional view in a normal observation state.
Figure 4B:
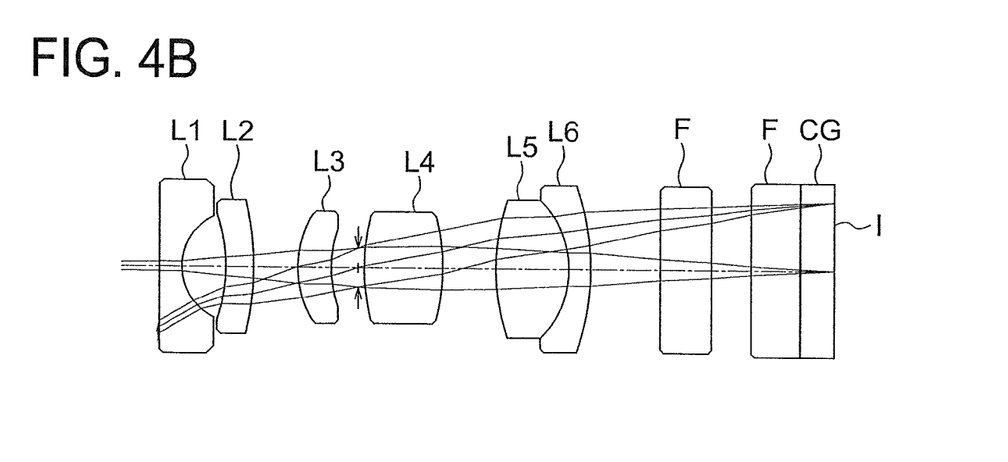
FIG. 4B is a cross-sectional view in a close observation state.
Figure 5A:
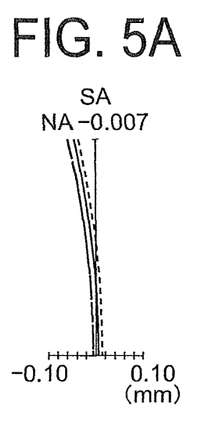
FIG. 5A, FIG. 5B, FIG. 5C, FIG. 5D, FIG. 5E, FIG. 5F, FIG. 5G, and FIG. 5H are aberration diagrams showing a spherical aberration (SA), an astigmatism (AS), a distortion (DT), and a chromatic aberration of magnification (CC) respectively, of the example 2.
Figure 5B:
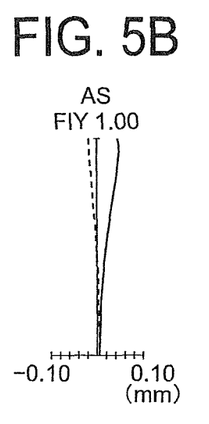
Figure 5C:
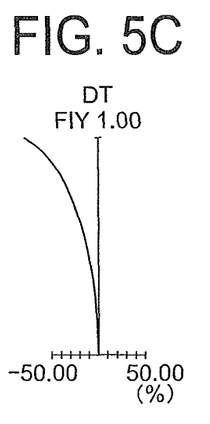
Figure 5D:
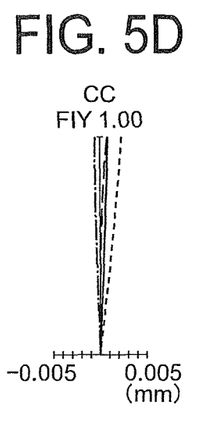
Figure 5E:
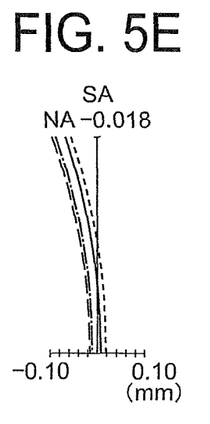
Figure 5F:
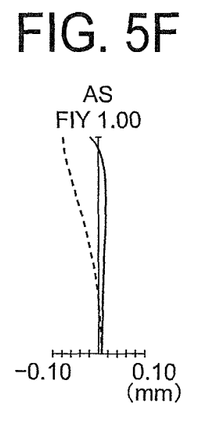
Figure 5G:
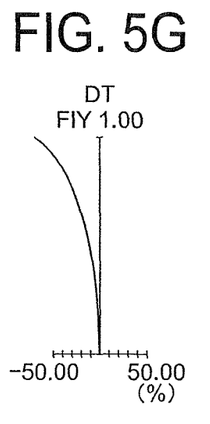
Figure 5H:
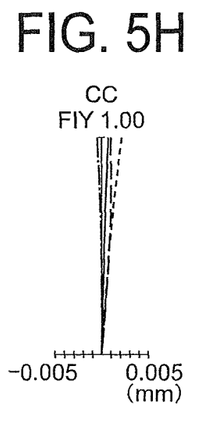

FIG. 4A is a cross-sectional view in a normal observation state (object point at a long distance) of the objective optical system for endoscope according to the present example, and FIG. 4B is a cross-sectional view in a close observation state (object point at a close distance) of the objective optical system for endoscope according to the present example.

In the example 2, widening of angle is realized by an arrangement similar as in the abovementioned example 1.

The arrangement includes in order from an object side, a first negative lens L1 which is planoconcave, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red absorbing filter F, a cover glass F, and a COD cover glass CG.

The fifth positive lens L5 and the sixth negative meniscus lens L6 are cemented. Moreover, the cover glass F and the COD cover glass CG are cemented. Moreover, a YAG laser cut coating is applied to an object side of the infra-red absorbing filter and an LD laser cut coating is applied to an image side of the infra-red absorbing filter. Furthermore, the third positive meniscus lens L3 moves toward the image (image plane I) side at the time of focusing from the normal observation state (FIG. 4A) to the close observation state (FIG. 4B).

FIG. 5A, FIG. 5B, FIG. 5C, and FIG. 5D show a spherical aberration (SA), an astigmatism (AS), a distortion (DT), and a chromatic aberration of magnification (CC) in the normal observation state of the present example.

FIG. 5E, FIG. 5F, FIG. 5G, and FIG. 5H show a spherical aberration (SA), an astigmatism (AS), a distortion (DT), and a chromatic aberration of magnification (CC) in the close observation state of the present example.

Example 3

An objective optical system for endoscope according to an example 3 will be described below.

Figure 6A:
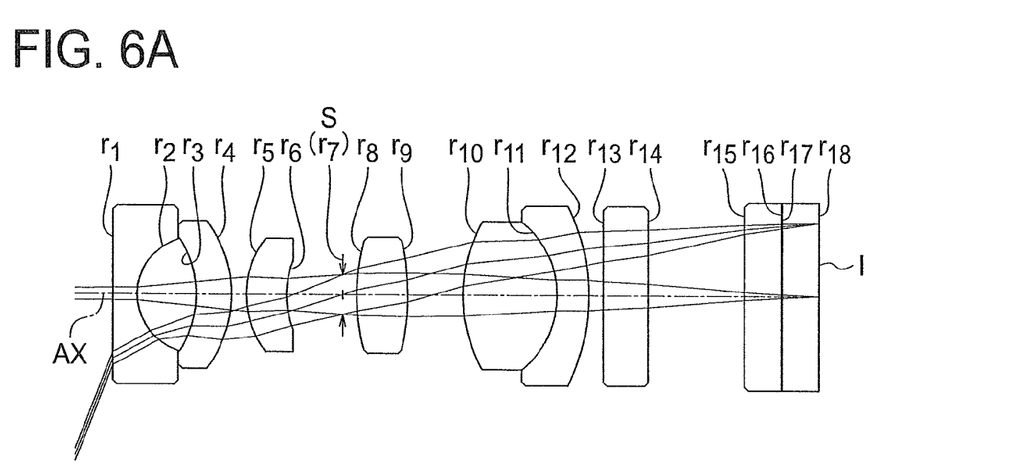
FIG. 6A is a cross-sectional view in a normal observation state.
Figure 6B:
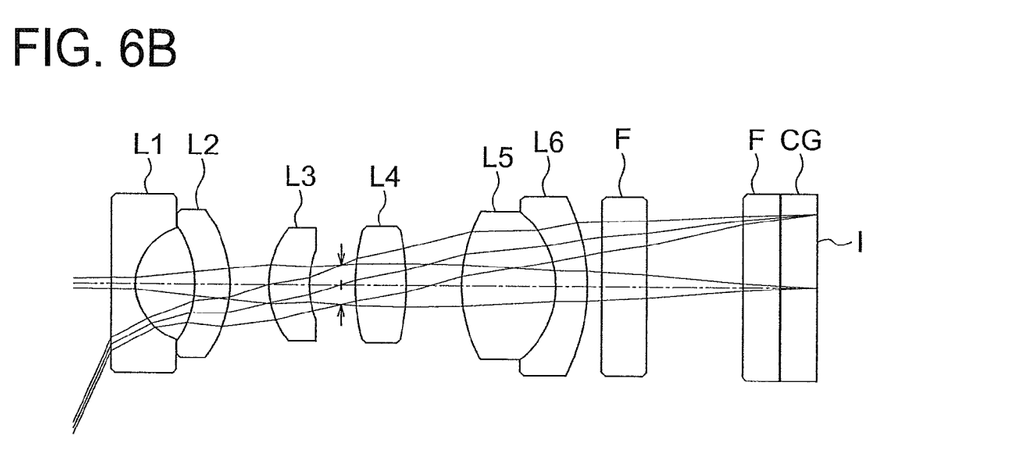
FIG. 6B is a cross-sectional view in a close observation state.
Figure 7A:
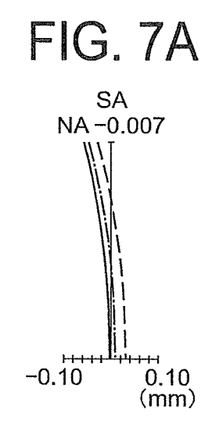
FIG. 7A, FIG. 7B, FIG. 7C, FIG. 7D, FIG. 7E, FIG. 7F, FIG. 7G, and FIG. 7H are aberration diagrams showing a spherical aberration (SA), an astigmatism (AS), a distortion (DT), and a chromatic aberration of magnification (CC) respectively, of the example 3.
Figure 7B:
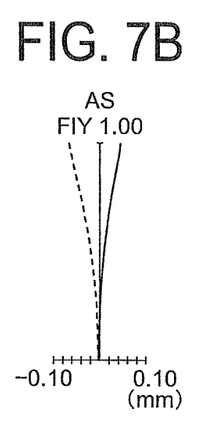
Figure 7C:
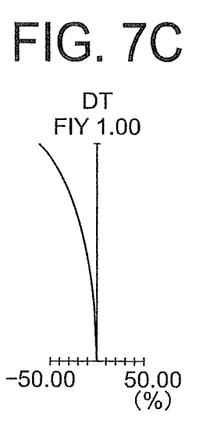
Figure 7D:
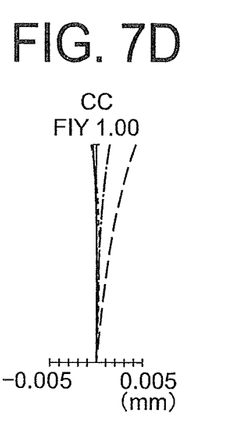
Figure 7E:
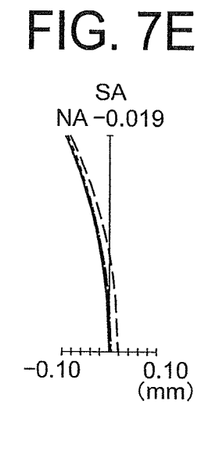
Figure 7F:
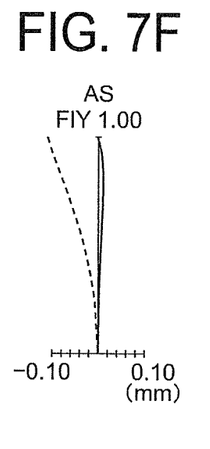
Figure 7G:
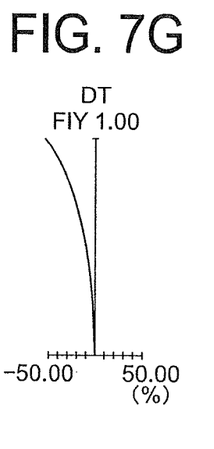
Figure 7H:
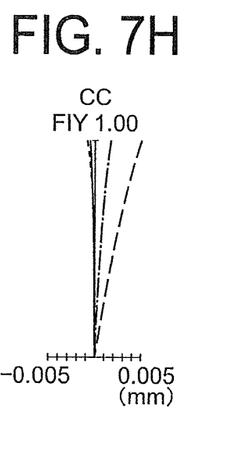

FIG. 6A is a cross-sectional view in a normal observation state (object point at a long distance) of the objective optical system for endoscope according to the present example, and FIG. 6B is a cross-sectional view in a close observation state (object point at a close distance) of the objective optical system for endoscope according to the present example.

Similar to the example 1, in the example 3, an arrangement includes in order from an object side, a first negative lens L1 which is planoconcave, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red filter F, a cover glass F, and a CCD cover glass CG.

The fifth positive lens L5 and the sixth negative meniscus lens L6 are cemented. Moreover, the cover glass F and the COD cover glass CG are cemented. Moreover, an LD laser cut coating is applied to an object side of the infra-red absorbing filter and a YAG laser cut coating is applied to an image side of the infra-red absorbing filter. Furthermore, the third positive meniscus lens L3 moves toward the image (image plane I) side at the time of focusing from the normal observation state (FIG. 6A) to the close observation state (FIG. 6B).

FIG. 7A, FIG. 7B, FIG. 7C, and FIG. 7D show a spherical aberration (SA), an astigmatism (AS), a distortion (DT), and a chromatic aberration of magnification (CC) in the normal observation state of the present example.

FIG. 7E, FIG. 7F, FIG. 7G, and FIG. 7H show a spherical aberration (SA), an astigmatism (AS), a distortion (DT), and a chromatic aberration of magnification (CC) in the close observation state of the present example.

Example 4

An objective optical system for endoscope according to an example 4 will be described below.

Figure 8A:
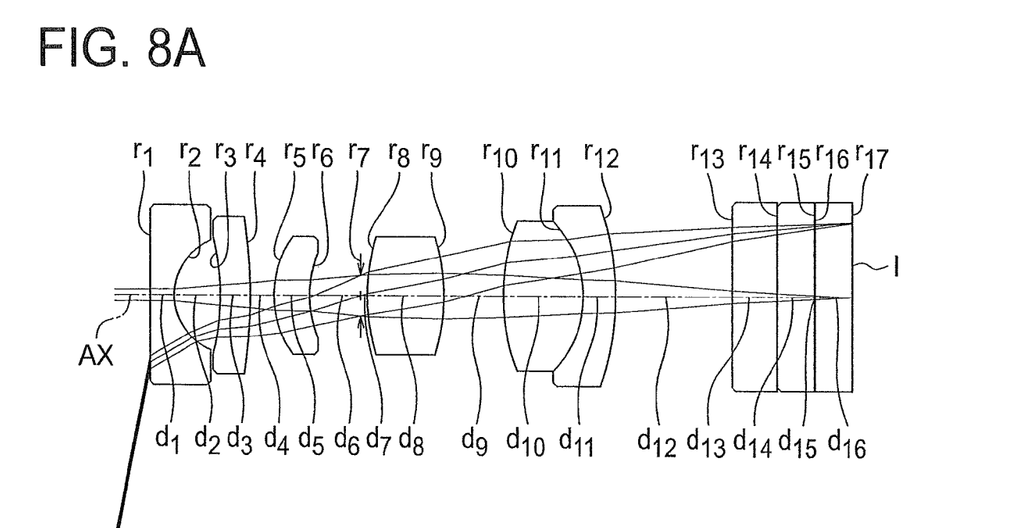
FIG. 8A is a cross-sectional view in a normal observation state.
Figure 8B:
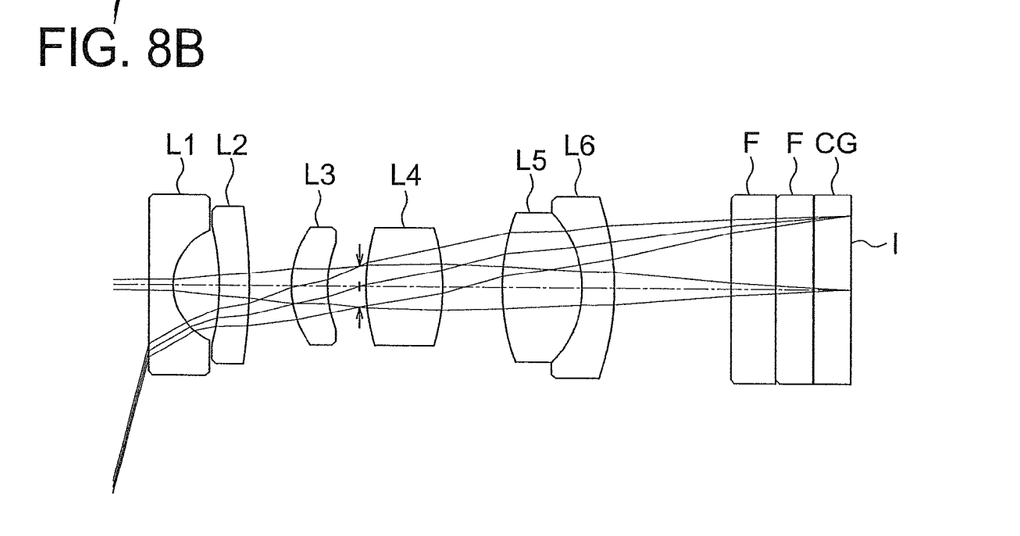
FIG. 8B is a cross-sectional view in a close observation state.
Figure 9A:
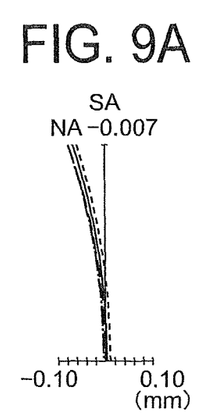
FIG. 9A, FIG. 9B, FIG. 9C, FIG. 9C, FIG. 9E, FIG. 9F, FIG. 9G, and FIG. 9H are aberration diagrams showing a spherical aberration (SA), an astigmatism (AS), a distortion (DT), and a chromatic aberration of magnification (CC) respectively, of the example 4.
Figure 9B:
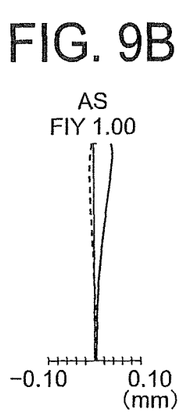
Figure 9C:
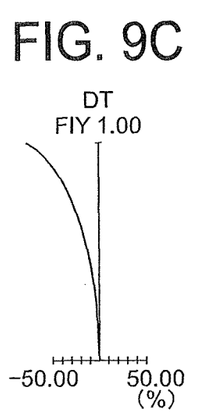
Figure 9D:
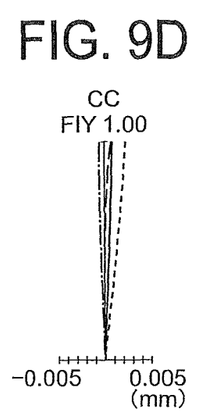
Figure 9E:
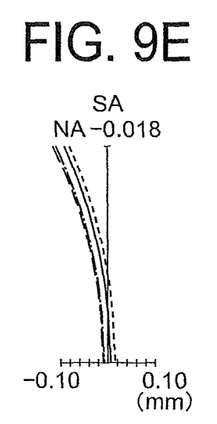
Figure 9F:
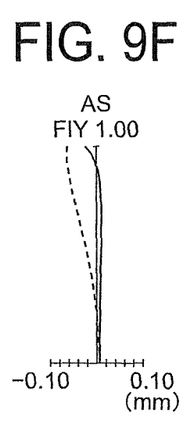
Figure 9G:
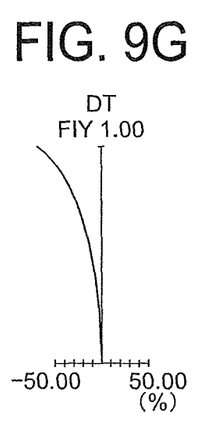
Figure 9H:
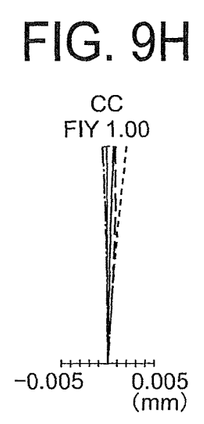

FIG. 8A is a cross-sectional view in a normal observation state (object point at a long distance) of the objective optical system for endoscope according to the preset example, and FIG. 8B is a cross-sectional view in a close observation state (object point at a close distance) of the objective optical system for endoscope according to the present example.

Similar to the example 2, in the example 4, an arrangement includes in order from an object side, a first negative lens L1 which is planoconcave, a second negative meniscus lens L2 having a convex surface directed toward an image side, a third positive meniscus lens L3 having a convex surface directed toward the object side, an aperture stop S, a fourth positive lens L4 which is biconvex, a fifth positive lens L5 which is biconvex, a sixth negative meniscus lens L6 having a convex surface directed toward the image side, an infra-red absorbing filter F, a cover glass F, and a COD cover glass CG.

The fifth positive lens L5 and the sixth negative meniscus lens L6 are cemented. Moreover, the cover glass F and the COD cover glass CG are cemented. Moreover, an LD laser cut coating is applied to an object side of the infra-red absorbing filter and a YAG laser cut coating is applied to an image side of the infra-red absorbing filter. Furthermore, the third positive meniscus lens L3 moves toward the image (image plane I) side at the time of focusing from the normal observation state (FIG. 8A) to the close observation state (FIG. 8B).

FIG. 9A, FIG. 9B, FIG. 9C, and FIG. 9D show a spherical aberration (SA), an astigmatism (AS), a distortion (DT), and a chromatic aberration of magnification (CC) in the normal observation state of the present example.

FIG. 9E, FIG. 9F, FIG. 9G, and FIG. 9H show a spherical aberration (SA), an astigmatism (AS), a distortion (DT), and a chromatic aberration of magnification (CC) in the close observation state of the present example.

Numerical data for the examples is shown below. Regarding the symbols, r denotes a radius of curvature of each lens surface, d denotes a distance between lens surfaces, nd denotes a refractive index for a d-line of each lens, vd denotes Abbe's number for each lens, Eno denotes an F-number, ω denotes a half angle of view, and IH denotes an image height.

Example 1

Unit nun

Surface data

| Surface no. | r | d | nd | vd |
| --- | --- | --- | --- | --- |
| 1 | ∞ | 0.320 | 1.88300 | 40.76 |
| 2 | 0.9087 | 0.7537 | | |
| 3 | −1.2930 | 0.4800 | 1.88300 | 40.76 |
| 4 | −1.5764 | d4 | | |
| 5 | 1.4374 | 0.5400 | 1.88300 | 40.76 |
| 6 | 1.5329 | d6 | | |
| 7(Stop) | ∞ | 0.1910 | | |
| 8 | 2.6879 | 1.0600 | 1.51633 | 64.14 |
| 9 | −2.6879 | 0.7537 | | |
| 10 | 2.8896 | 1.2000 | 1.48749 | 70.23 |
| 11 | −1.4034 | 0.4200 | 1.92286 | 18.90 |
| 12 | −2.6879 | 0.9999 | | |
| 13 | ∞ | 0.6000 | 1.52100 | 65.13 |
| 14 | ∞ | 0.5000 | 1.51633 | 64.14 |
| 15 | ∞ | 0.0100 | 1.51300 | 64.00 |
| 16 | ∞ | 0.5000 | 1.61062 | 50.49 |
| Image plane | ∞ | | | |

Various data

| | normal observation state | close observation state |
| --- | --- | --- |
| focal length | 1.072 | 1.056 |
| object distance | 12.5 | 4.5 |
| Fno | 5.94 | 5.95 |
| ω | 67.2 | 66.0 |
| IH | 1 | 1 |
| d4 | 0.1730 | 0.4809 |
| d6 | 0.7325 | 0.4246 |

Example 2

Unit mm

Surface data

| Surface no. | r | d | nd | νd |
|---|---|---|---|---|
| 1 | ∞ | 0.3200 | 1.88300 | 40.76 |
| 2 | 0.8291 | 0.6274 | | |
| 3 | -2.4204 | 0.4000 | 1.88300 | 40.76 |
| 4 | -4.3174 | d4 | | |
| 5 | 1.5329 | 0.4800 | 1.64769 | 33.79 |
| 6 | 1.7898 | d6 | | |
| 7(Stop) | ∞ | 0.0860 | | |
| 8 | 3.0870 | 1.1600 | 1.62004 | 36.26 |
| 9 | -3.0870 | 0.7750 | | |
| 10 | 3.0998 | 1.0600 | 1.58913 | 61.14 |
| 11 | -1.4374 | 0.3200 | 1.92286 | 18.90 |
| 12 | -3.7166 | 1.0000 | | |
| 13 | ∞ | 0.7431 | 1.52100 | 65.13 |
| 14 | ∞ | 0.5854 | | |
| 15 | ∞ | 0.700 | 1.51633 | 64.14 |
| 16 | ∞ | 0.0100 | 1.51300 | 64.00 |
| 17 | ∞ | 0.5000 | 1.61062 | 50.49 |
| Image plane | ∞ | 0.0000 | | |

Various data

| | normal observation state | close observation state |
|---|---|---|
| focal length | 0.998 | 0.990 |
| object distance | 11.5 | 4.0 |
| Fno | 6.00 | 6.02 |
| ω | 80.5 | 76.5 |
| IH | 1 | 1 |
| d4 | 0.3216 | 0.6444 |
| d6 | 0.7229 | 0.4002 |

Example 3

Unit mm

Surface data

| Surface no. | r | d | nd | νd |
|---|---|---|---|---|
| 1 | ∞ | 0.3185 | 1.88300 | 40.76 |
| 2 | 0.8075 | 0.7856 | | |
| 3 | -1.4551 | 0.4706 | 1.88300 | 40.76 |
| 4 | -1.7058 | d4 | | |
| 5 | 1.2793 | 0.5400 | 1.88300 | 40.76 |
| 6 | 1.2840 | d6 | | |
| 7(Stop) | ∞ | 0.1911 | | |
| 8 | 2.8681 | 0.6950 | 1.48749 | 70.23 |
| 9 | -3.3606 | 0.7488 | | |
| 10 | 2.0631 | 1.2700 | 1.48749 | 70.23 |
| 11 | -1.3083 | 0.4250 | 1.92286 | 18.90 |
| 12 | -2.7838 | 0.1900 | | |
| 13 | ∞ | 0.6000 | 1.52100 | 65.13 |
| 14 | ∞ | 1.2918 | | |
| 15 | ∞ | 0.5000 | 1.51633 | 64.14 |
| 16 | ∞ | 0.0100 | 1.51300 | 64.00 |
| 17 | ∞ | 0.5000 | 1.61062 | 50.49 |
| Image plane | ∞ | | | |

Various data

| | normal observation state | close observation state |
|---|---|---|
| focal length | 1.087 | 1.075 |
| object distance | 12.7 | 4.1 |
| Fno | 6.09 | 6.11 |
| ω | 68.6 | 66.0 |
| IH | 1 | 1 |
| d4 | 0.2014 | 0.5257 |
| d6 | 0.7521 | 0.4280 |

Example 4

Unit mm

Surface data

| Surface no. | r | d | nd | νd |
|---|---|---|---|---|
| 1 | ∞ | 0.3200 | 1.88300 | 40.76 |
| 2 | 0.8134 | 0.6081 | | |
| 3 | -3.3652 | 0.4000 | 1.88300 | 40.76 |
| 4 | -7.0620 | d4 | | |
| 5 | 1.3621 | 0.4800 | 1.64769 | 33.79 |
| 6 | 1.6153 | d6 | | |
| 7(Stop) | ∞ | 0.0850 | | |
| 8 | 2.7557 | 1.0360 | 1.58144 | 40.75 |
| 9 | -2.7539 | 0.7967 | | |
| 10 | 2.9158 | 1.0700 | 1.58913 | 61.14 |
| 11 | -1.4447 | 0.4250 | 1.92286 | 18.90 |
| 12 | -3.8660 | 1.5479 | | |
| 13 | ∞ | 0.6000 | 1.52100 | 65.13 |
| 14 | ∞ | 0.5000 | 1.51633 | 64.14 |
| 15 | ∞ | 0.0100 | 1.51300 | 64.00 |
| 16 | ∞ | 0.5000 | 1.61062 | 50.49 |
| Image plane | ∞ | | | |

Various data

| | normal observation state | close observation state |
|---|---|---|
| focal length | 1.005 | 0.995 |
| object distance | 11.4 | 4.0 |
| Fno | 5.90 | 5.92 |
| ω | 79.5 | 76.1 |
| IH | 1 | 1 |
| d4 | 0.3185 | 0.5666 |
| d6 | 0.6770 | 0.4289 |

Numerical values for conditional expressions (1) to (9) of the objective optical system for endoscopes according to the example 1, the example 2, the example 3, and the example 4 are shown below. Numerical values in the first line for conditional expression (3) are numerical values in the normal observation state, and numerical values in the second line for conditional expression (3) are numerical values in the close observation state.

Conditional expression

| | Example1 | Example2 | Example3 | Example4 |
|---|---|---|---|---|
| (1) | 2.78 | 2.67 | 3.28 | 2.53 |
| (2) | -1.02 | -0.93 | -0.91 | -0.92 |
| (3) | -1.51 | -0.99 | -1.24 | -1.00 |
| | -1.53 | -1.00 | -1.26 | -1.01 |
| (4-1) | -0.70 | -0.34 | -0.55 | -0.24 |
| (4-2) | -0.58 | -0.19 | -0.47 | -0.12 |
| (5) | 0.57 | 0.54 | 0.77 | 0.52 |
| (6) | -2.23 | -2.29 | -2.50 | -2.26 |
| (7) | 23.1 | 29.2 | 22.1 | 30.7 |
| (8) | 1.73 | 1.67 | 1.78 | 1.65 |
| (9) | 5.94 | 6.00 | 6.09 | 5.90 |

Various embodiments of the present invention have been described above. However, the present invention is not limited to these embodiments, and embodiments which are arranged by combining appropriately these embodiments, without departing from the scope of the invention, are also included in the present invention.

As described above, the present invention is useful for an objective optical system for endoscope which is small-sized, and has a favorable optical performance.

The present invention shows an effect that an objective optical system for endoscope according an embodiment of the present invention is small-sized and has a favorable optical performance.

What is claimed is:

1. An objective optical system for an endoscope comprising in order from an object side:
   a first negative lens which is planoconcave;
   a second meniscus lens having a convex surface directed toward an image side;
   a third positive meniscus lens having a convex surface directed toward the object side;
   a positive lens unit; and
   a cemented lens in which, a positive lens and a negative lens are cemented, wherein
   focusing is carried out by moving the third positive meniscus lens along an optical axis, and
   the second meniscus lens is a negative lens, and
   wherein negative and positive refers to a refractive power, and
   the objective optical system for endoscope satisfies the following conditional expression (1), and satisfies at least one of the following conditional expressions (4-1) and (4-2)

$$2.3 \leq fp/Ih \leq 5 \quad (1)$$

$$-1.5 \leq r2/r3 \leq -0.28 \quad (4\text{-}1)$$

$$-0.2 \leq r2/r4 \leq -0.08 \quad (4\text{-}2)$$

where,
   fp denotes a focal length of the positive lens unite and
   Ih denotes the maximum image height of the objective optical system for endoscope,
   r2 denotes an image-side radius of curvature of the first negative lens,
   r3 denotes an object-side radius of curvature of the second meniscus lens, and
   r4 denotes an image-side radius of curvature of the second meniscus lens.

2. The objective optical system for endoscope according to claim 1, wherein the objective optical system for endoscope satisfies the following conditional expression (2)

$$-2 \leq f1/Ih \leq -0.9 \quad (2)$$

where,
   f1 denotes a focal length of the first negative lens, and
   Ih denotes the maximum image height of the objective optical system for endoscope.

3. The objective optical system for endoscope according to claim 1, wherein the objective optical system for endoscope satisfies the following conditional expression (3)

$$-3 \leq (fc1 \times fc2)/(fc \times f) \leq -0.85 \quad (3)$$

where,
   fc1 denotes a focal length of the positive lens in the cemented lens,
   fc2 denotes a focal length of the negative lens in the cemented lens,
   fc denotes a combined focal length of the cemented lens, and
   f denotes a focal length of the overall objective optical system in a normal observation state or in a close observation state for endoscope.

4. The objective optical system for endoscope according to claim 1, wherein the objective optical system for endoscope satisfies the following conditional expression (5)

$$0.45 \leq fp/fc \leq 1.3 \quad (5)$$

where,
   fp denotes the focal length of the positive lens unit, and
   fc denotes a combined focal length of the cemented lens.

5. The objective optical system for endoscope according to claim 1, wherein the objective optical system for endoscope satisfies the following conditional expression (6)

$$-5 \leq fpc/f1 \leq -2 \quad (6)$$

where,
   fpc denotes a combined focal length of the positive lens unit and the cemented lens, and
   f1 denotes a focal length of the first negative lens.

6. The objective optical system for endoscope according to claim 1, wherein the objective optical system for endoscope satisfies the following conditional expression (7)

$$22 \leq f3/df \leq 50 \quad (7)$$

where,
   f3 denotes a focal length of the third positive meniscus lens, and
   df denotes the maximum amount of movement of the third positive meniscus lens.

7. The objective optical system for endoscope according to claim 1, wherein the objective optical system for endoscope satisfies the following conditional expression (8)

$$1.35 \leq \Sigma d(L1-L3)/Ih \leq 3 \quad (8)$$

where,
   $\Sigma d$ (L1–L3) denotes the minimum axial distance from an object-side surface of the first negative lens up to an object-side surface of the third positive meniscus lens, and
   Ih denotes the maximum image height of the objective optical systemfor endoscope.

8. The objective optical system for endoscope according to claim 1, wherein the objective optical system for endoscope satisfies the following conditional expression (9)

$$4 \leq Fno \leq 7 \quad (9)$$

where,
   Fno denotes an F-number for the objective optical system for endoscope.

9. The objective optical system for endoscope according to claim 1, wherein only the third positive meniscus lens moves at the time of focusing.

10. The objective optical system for endoscope according to claim 1, wherein an aperture stop is disposed on the image side of the third positive meniscus lens.

* * * * *